US009383197B2

(12) United States Patent
Meschter et al.

(10) Patent No.: US 9,383,197 B2
(45) Date of Patent: Jul. 5, 2016

(54) SYSTEM AND METHOD FOR MEASURING COOLING OF A COMPONENT (71) Applicant: General Electric Company, Schenectady, NY (US)

(72) Inventors: Peter Joel Meschter, Franklin, TN (US); Lawrence Bernard Kool, Clifton Park, NY (US); James Albert Tallman, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 93 days.

(21) Appl. No.: 14/512,613

(22) Filed: Oct. 13, 2014

(65) Prior Publication Data

US 2016/0102974 A1 Apr. 14, 2016

(51) Int. Cl.

| G01B 15/02 | (2006.01) |
|---|---|
| G01N 23/22 | (2006.01) |
| G01N 23/225 | (2006.01) |
| G01N 23/20 | (2006.01) |
| C23C 16/34 | (2006.01) |
| C23C 16/40 | (2006.01) |
| C23C 14/24 | (2006.01) |
| C23C 14/06 | (2006.01) |
| C23C 14/08 | (2006.01) |

(52) U.S. Cl.
CPC .......... *G01B 15/02* (2013.01); *C23C 14/0641* (2013.01); *C23C 14/08* (2013.01); *C23C 14/24* (2013.01); *C23C 16/34* (2013.01); *C23C 16/40* (2013.01); *G01N 23/20* (2013.01); *G01N 23/22* (2013.01); *G01N 23/2252* (2013.01)

(58) Field of Classification Search
CPC ..................................................... G01B 15/02
See application file for complete search history.

(56) References Cited

U.S. PATENT DOCUMENTS

| 4,774,150 A | 9/1988 | Amano et al. |
| 7,078,073 B2 | 7/2006 | Rigney et al. |
| 7,094,444 B2 | 8/2006 | Rigney et al. |
| 7,175,720 B2 | 2/2007 | Schnell et al. |
| 7,918,141 B1 | 4/2011 | Sathish et al. |
| 8,056,407 B2 | 11/2011 | Bagnall et al. |

(Continued)

OTHER PUBLICATIONS

Carapelle et al.,"Portable x-ray fluorescence spectrometer for coating thickness measurement", Review of Scientific Instruments, AIP Scitations, 2007, vol. 78, Issue 12, pp. 123109-1-123109-3.
Russe et al.,"Validation of Terahertz Coating Thickness Measurements Using X-ray Microtonnography", Mol. Pharmaceutics, ACS publications, 2012,9 (12), pp. 3551-3559.
Jain et al.,"An X-ray fluorescence method for coating thickness measurement", X-Ray Spectrometry, Wiley Online Library, Jan. 1979, vol. 8, Issue 1, pp. 11-13.

(Continued)

*Primary Examiner* — Christine Sung
(74) *Attorney, Agent, or Firm* — John P. Darling (57) ABSTRACT

A system and method for measuring cooling effectiveness of a component is disclosed. The method includes providing a component having a surface provided with a coating including a volatilization-susceptible constituent and a volatilization-resistant constituent. Further, the method includes supplying a first gaseous medium over the surface of the component through a plurality of holes in the component and feeding a second gaseous medium along the surface of the component. The method includes exposing the surface of the component to the first and second gaseous mediums for a predetermined period. The method further includes determining a thickness of the coating exposed to the flow of the first and second gaseous mediums. The method includes analyzing the thickness of the coating to determine whether the coating is removed from the surface of the component upon exposure to the first and second gaseous mediums.

24 Claims, 5 Drawing Sheets

(56) References Cited

U.S. PATENT DOCUMENTS

| | | | |
|---|---|---|---|
| 9,250,188 B2* | 2/2016 | Tallman | G01N 21/77 |
| 2010/0072072 A1 | 3/2010 | Beckel et al. | |
| 2011/0119020 A1* | 5/2011 | Key | G01J 5/00 |
| | | | 702/135 |
| 2011/0164653 A1* | 7/2011 | Allen | G01N 25/72 |
| | | | 374/43 |

OTHER PUBLICATIONS

Byeon et al.,"Non-destructive evaluation of degradation in multi-layered thermal barrier coatings by electrochemical impedance spectroscopy", Materials Science and Engineering: A, ScienceDirect, Oct. 25, 2005, vol. 407, pp. 213-225.

T.D.T. Latter.,"X-Ray Fluorescence for Coating Thickness Measurement", Circuit World, Emerald Insight, 1983, vol. 10 Iss: 1, pp. 20-25.

* cited by examiner

FIG. 5

SYSTEM AND METHOD FOR MEASURING COOLING OF A COMPONENT

BACKGROUND

The present disclosure relates generally to measuring cooling of a component and more particularly, to a system and method for measuring cooling effectiveness of the component.

A method of cooling an engine component includes providing an array of cooling holes on a surface of a component to enable formation of a cooling film that prevents overheating of the component during engine operation, for example. The effectiveness of an array of cooling holes in dispersing a cooling medium across the surface of a component is typically analyzed using known fluid computational methods. However, these methods have limitations in modeling the film cooling effectiveness accurately. Accurate fluid computational methods may require finite element grids on the surface of the component, which in turn requires long computation times and significant expenses to model temperature distribution on the film cooled surface.

A direct method of measuring cooling effectiveness of the component includes providing a thermocouple array on the surface of the component or pyrometer scanner to measure the surface temperature distribution. Such direct methods may require multiple thermocouples or a complex pyrometric system. Such measurement systems may not be capable of measuring the surface temperature distribution on the component at the desired resolution.

Thus, there is a need for an improved system and method for measuring effectiveness of cooling of a component.

BRIEF DESCRIPTION

In accordance with one exemplary embodiment, a method for measuring cooling effectiveness of a component is disclosed. The method includes providing the component having a surface provided with a coating including a volatilization-susceptible constituent and a volatilization-resistant constituent. Further, the method includes supplying a first gaseous medium through a plurality of holes in the component for forming a cooling film of the first gaseous medium on the surface of the component. The method further includes feeding a second gaseous medium along the surface of the component and exposing the component to a flow of the first and second gaseous mediums for a predetermined period. The method further includes determining a thickness of the coating exposed to the flow of the first and second gaseous mediums from a measurement device. Further, the method includes analyzing the thickness to determine whether at least a portion of the coating is removed from the surface of the component upon exposure to the first and second gaseous mediums for the predetermined period. A retained thickness of the coating at any region on the surface is indicative of the efficacy of film cooling. The removal of most or all of the coating thickness is indicative of relatively ineffective film cooling and the retention of most or all of the coating thickness is indicative of relatively effective film cooling.

In accordance with another exemplary embodiment, a method for measuring cooling effectiveness is disclosed. The method includes providing a component having a surface provided with a coating including a volatilization-susceptible constituent and a volatilization-resistant constituent. Further, the method includes supplying a first gaseous medium through a plurality of holes in the component for a predetermined period so as to form a cooling film of the first gaseous medium on the surface. The method further includes feeding a second gaseous medium along the surface of the component for the predetermined period so as to remove at least a portion of the coating upon exposure to the second gaseous medium. Further, the method includes determining a thickness of the coating exposed to a flow of the first and second gaseous mediums for the predetermined period. The method further includes analyzing the thickness of the coating, in which a retained thickness of the coating at any region on the surface is indicative of the efficacy of film cooling. The removal of most or all of the coating thickness is indicative of relatively ineffective film cooling and the retention of most or all of the coating thickness is indicative of relatively effective film cooling.

In accordance with one exemplary embodiment, a system for measuring cooling effectiveness is disclosed. The system includes a first source for supplying a first gaseous medium through a plurality of holes in a component having a surface provided with a coating including a volatilization-susceptible constituent and a volatilization-resistant constituent. Further, the system includes a second source for supplying a second gaseous medium along the surface of the component and measurement device for determining a thickness of the coating exposed to a flow of the first and second gaseous mediums for a predetermined period. The system further includes a processor-based device communicatively coupled to the measurement device to receive the thickness of the coating and analyze the obtained thickness. The analysis includes determining whether at least a portion of the coating is removed from the surface of the component upon exposure to the first and second gaseous mediums. A retained thickness of the coating at any region on the surface is indicative of the efficacy of film cooling. The removal of most or all of the coating thickness is indicative of relatively ineffective film cooling and the retention of most or all of the coating thickness is indicative of relatively effective film cooling.

DRAWINGS

These and other features and aspects of embodiments of the present disclosure will become better understood when the following detailed description is read with reference to the accompanying drawings in which like characters represent like parts throughout the drawings, wherein:

FIG. 2 is a schematic view of a system used for measuring cooling effectiveness of the component in accordance with the exemplary embodiment of FIG. 1a;

FIG. 4b is a schematic view of a redesigned component exposed to the flow of the first and second gaseous mediums in accordance with the exemplary embodiments of FIGS. 1a, 2, 3, and 4a.

DETAILED DESCRIPTION

Embodiments discussed herein disclose a new improved system and method for measuring cooling effectiveness of a component having holes, for example cooling holes, disposed along a flow path of the component such as an engine component. The holes are configured to provide a cooling film of a first gaseous medium such as air for preventing overheating of the component over a surface of the component provided with a coating. The flow path of the component is configured to receive a second gaseous medium such as a combustion gas for volatilizing at least a portion of the coating which is not effectively covered by the cooling film. The coating provided on the component may be evaluated by a measurement device for determining a thickness of the coating exposed to a flow of the first and second gaseous mediums. The determined thickness of the coating is analyzed via a processor-based device for determining whether at least the portion of the coating is removed from the surface of the component upon exposure to the flow of the first and second gaseous mediums. In one embodiment, a retained thickness of the coating at any region on the surface is indicative of the efficacy of film cooling. The removal of most or all of the coating thickness is indicative of relatively ineffective film cooling and a retention of most or all of the coating thickness is indicative of relatively effective film cooling.

Figure 1A:
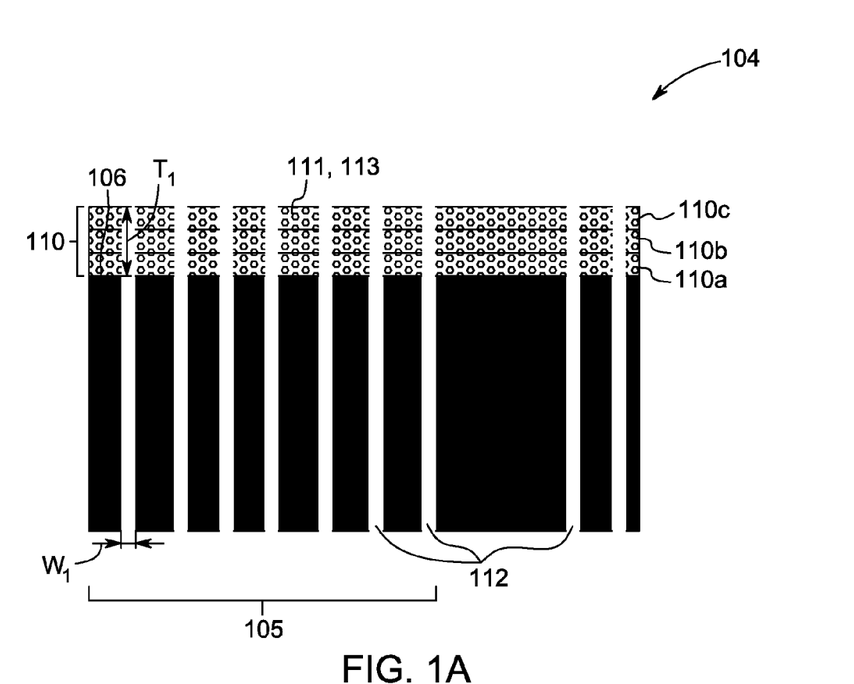
FIG. 1a is a schematic view of a component having a surface provided with a coating in accordance with one exemplary embodiment.

FIG. 1a is a schematic view of a component 104 in accordance with one exemplary embodiment of the present invention. The component 104 is represented from a side view. The component 104 may be part of a larger system, for example, a gas turbine engine, a jet engine, and the like. The component 104, in one example, is an aircraft engine component. In certain other embodiments, the component 104 may be a gas engine component, a turbine component, an airfoil, a test specimen, a prototype component, and the like. In some other embodiments, the component 104 may be a combustor liner, a blade (bucket), a vane (nozzle), a shroud, and the like.

The component 104 includes a coating 110 disposed on a surface 106 of the component 104. In one embodiment, the surface 106 is an outer surface of the component 104 that is exposed to a flow of first and second gaseous mediums (not shown in FIG. 1a). It should be noted herein that the exemplary coating 110 may be applicable to any suitable surface and any suitable component exposed to the flow of the first and second gaseous mediums. The coating 104 includes a volatilization-susceptible constituent 111 and a volatilization-resistant constituent 113. Concentrations of the volatilization-susceptible constituent 111 and the volatilization-resistant constituent 113 vary inversely to one another as a function of distance in the coating 110 measured from the surface 106 of the component 104. In one or more embodiments, a suitable volatilization-susceptible constituent includes a nitride of at least one of boron, chromium, silicon, nickel, cobalt, and iron and an oxide of at least one of boron, chromium, silicon, nickel, cobalt, and iron. Similarly, a suitable volatilization-resistant constituent includes an oxide of at least one of titanium, zirconium, hafnium, aluminum, yttrium, and a rare earth element.

The coating 110 is a multilayer coating having the concentration of volatilization-susceptible constituent 111 in a range from about ten percent to about ninety percent by volume and the concentration of volatilization-resistant constituent 113 in a range from about ninety percent to about ten percent by volume. In the multilayer coating, the concentrations of volatilization-susceptible constituent 111 and volatilization-resistant constituent 113 vary systematically over a thickness "$T_1$" of the coating 110 from the surface 106 of the component 104. In the illustrated embodiment, three layers of coating 110a, 110b, 110c are represented with inversely varying concentrations along the thickness "$T_1$". A first layer 110a may have the concentration of about thirty percent by volume of volatilization-susceptible constituent 111 and about seventy percent by volume of volatilization-resistant constituent 113. A second layer 110b may have the concentration of about sixty percent by volume of volatilization-susceptible constituent 111 and about forty percent by volume of volatilization-resistant constituent 113. A third layer may have the concentration of about ninety percent by volume of volatilization-susceptible constituent 111 and about ten percent by volume of volatilization-resistant constituent 113. It should be noted herein that the multilayer coating 110 may be applied by a suitable deposition method such as a chemical vapor deposition technique (CVD) or a physical vapor deposition technique (PVD).

The component 104 further includes a plurality of holes 112. In one example, each hole among the plurality of holes 112 has a diameter in a range from about one millimeter to about two millimeters. In one or more embodiments, suitable holes 112 may include cooling holes, leakage holes, and, backside airflow holes. In the illustrated embodiment, the plurality of holes 112 has a width "$W_1$" and is dispersed and/or located uniformly along a first region 105 of the component 104. The location and dimension of the plurality of holes 112 may vary depending on the application and design criteria. The plurality of holes 112 may be formed using suitable techniques such as drilling, milling, and the like. In one embodiment, the thickness "$T_1$" and width "$W_1$" are determined by a measurement device (not shown in FIG. 1a). The process of determination of the thickness "$T_1$" and width "$W_1$" via the measurement device are explained in greater detail below.

Figure 1B:
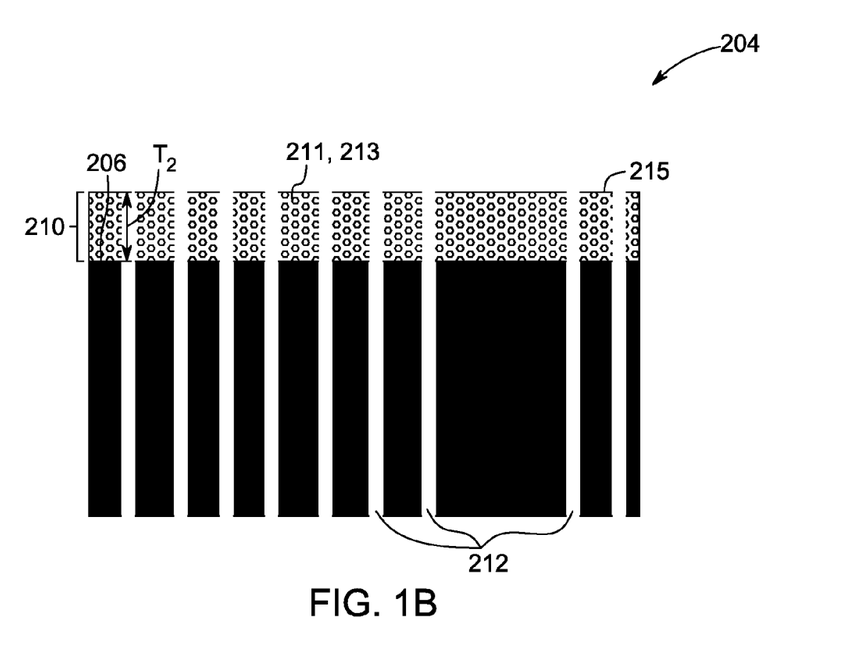
FIG. 1b is a schematic view of a component having a surface provided with a coating in accordance with another exemplary embodiment.

FIG. 1b is a schematic view of a component 204 in accordance with another exemplary embodiment of the present invention. The component 204 includes a coating 210 disposed on a surface 206 of the component 204. The coating 210 is a gradient coating having a concentration of volatilization-susceptible constituent 211 in a range from about ten percent to about ninety percent by volume and a concentration of volatilization-resistant constituent 213 in a range from about ninety percent to about ten percent by volume. The concentrations of the volatilization-susceptible constituent 211 and the volatilization-resistant constituent 213 in the graded coating 210 vary continuously through a thickness "$T_2$" of the coating 210.

In one embodiment, the graded coating 210 has the concentrations of about ten percent by volume of volatilization-susceptible constituent 211 and about ninety percent by volume of volatilization-resistant constituent 213 at the surface 206 of the component 204. Similarly, the graded coating 210 has the concentrations of about ninety percent by volume of volatilization-susceptible constituent 211 and about ten percent by volume of volatilization-resistant constituent 213 at a top surface 215 of the coating 210. The graded coating 210 may be applied by suitable deposition methods such as a chemical vapor deposition (CVD) technique or a physical vapor deposition (PVD) technique, and the like. The component 204 further includes a plurality of cooling holes 212 configured for providing a first gaseous medium onto the surface 206 of the component 204.

Figure 2:
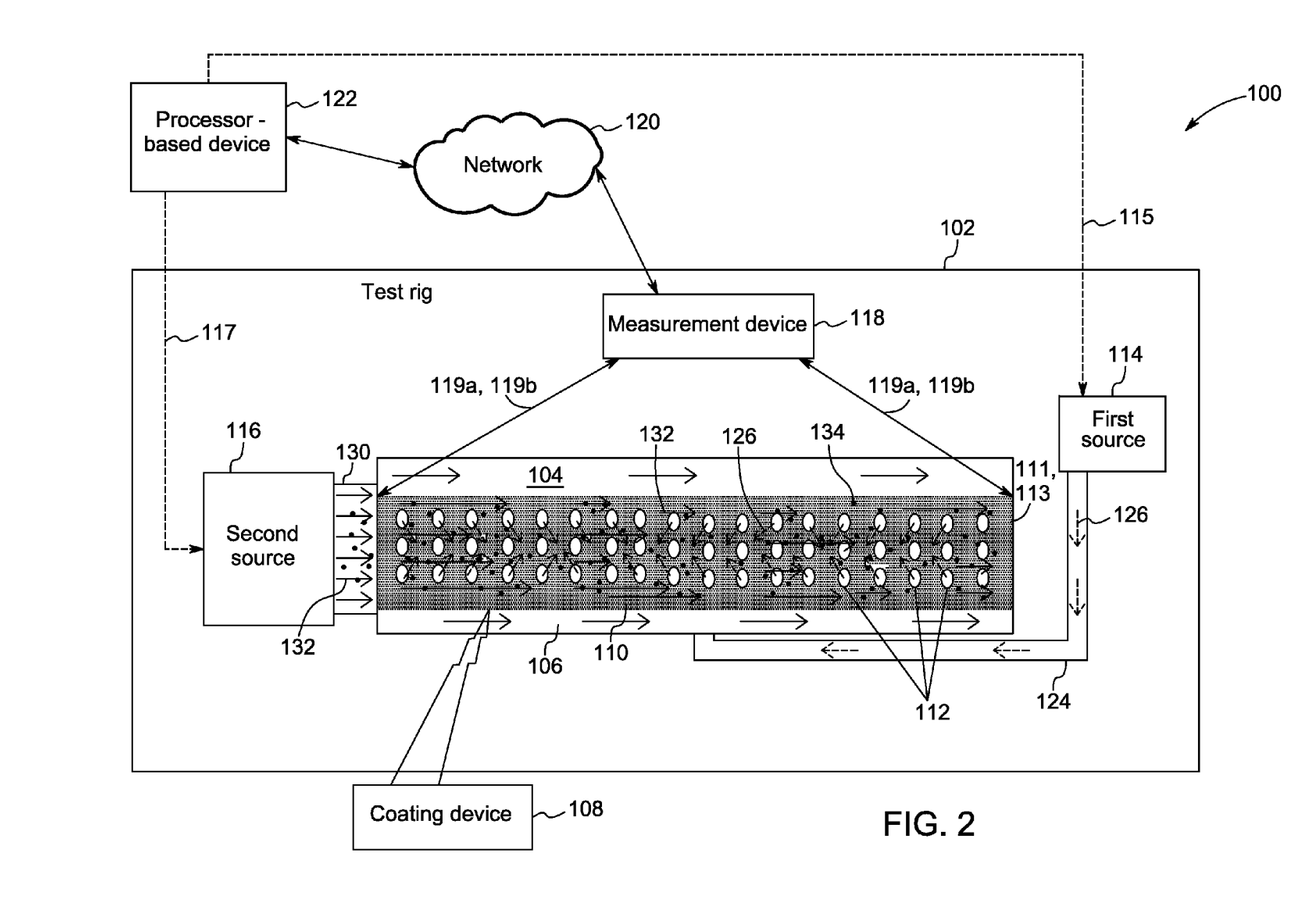

FIG. 2 is a schematic view of a system 100 for measuring cooling of the component 104 in accordance with one exemplary embodiment. The system 100 includes a test device 102, a coating device 108, a first source 114, a second source 116, a measurement device 118, and a processor-based device 122.

The test device 102 is typically a platform used for housing the component 104, the first source 114, and the second source 116. In the illustrated embodiment, the measurement device 118 is housed within the test device 102 and coating device 108 is disposed external to the test device 102. In certain other embodiments, the measurement device 118 may be disposed external to the test device 102 and coating device 108 may be housed within the test device 102. In one embodiment, the test device 102 may be a test rig and in certain other embodiments, the suitable test device 102 includes a furnace test apparatus, a turbine engine, or the like. In one embodiment, the test device 102 is deployed in a lab environment and/or in a test environment for determining cooling effectiveness of a prototype component. In certain other embodiments, the test device 102 may be deployed in a field environment for determining cooling effectiveness of an actual component. In one or more embodiments, suitable coating devices 108 include a chemical vapor deposition (CVD) device or a physical vapor deposition (PVD) device.

In one embodiment, the component 104 is disposed in the test device 102. The component 104 is represented from a top view. The component 104 includes the plurality of holes 112 for feeding a first gaseous medium 126 such as air, via the first source 114. During operation of the system 100, the first gaseous medium 126 is fed through the plurality of holes 112 to form a cooling film (not shown in FIG. 2) on the surface 106 of the component 104. The cooling film helps to prevent overheating of the component 104 and thereby prevent loss of mechanical properties of the component 104. Further, the surface 106 of the component 104 (i.e. flow path) is exposed to a flow of a second gaseous medium 132, such as a combustion gas provided by the second source 116.

The first gaseous medium 126 is a dry medium including at least one of air, nitrogen, and argon. The second gaseous medium 132 includes a reactant 134 and the first gaseous medium 126 does not include the reactant 134. In one embodiment, the reactant 134 includes at least one of oxygen, carbon dioxide, water vapor, and a species of gaseous halide. The species of gaseous halide may include fluorine, chlorine, bromine, or iodine. The second gaseous medium 132 may include water vapor in the range of one percent to hundred percent by volume. In one specific embodiment, the second gaseous medium 132 may include water vapor in the range of five percent to twenty percent by volume. It should be noted herein that the volatilization-susceptible constituent 111 of the coating 110 and the volatilization-resistant constituent 113 are removed uniformly if there is presence of the reactant 134 in the second gaseous medium 132. The volatilization-resistant constituent 113 breaks away from the surface 106 when enough of the volatilization-susceptible constituent 111 is removed by chemical reaction. In specific embodiment, the constituent 111 volatizes at a much faster rate in comparison with the constituent 113 upon exposure to the reactant for a predetermined period. In one embodiment, the volatilization-susceptible constituent 111 and volatilization-resistant constituent 113 are not volatilized in the presence of the cooling film of the first gaseous medium 126.

The first source 114 is coupled to the component 104 via a transfer line 124 and is configured to feed the first gaseous medium 126 to the component 104 via the transfer line 124. Specifically, the first gaseous medium 126 is fed onto the surface 106 of the component 104 through the plurality of holes 112. The first gaseous medium 126 forms the cooling film on the surface 106 of the component 104. In certain other embodiments, the first source 114 may have a valve (not shown in FIG. 2) for controlling a flow of the first gaseous medium 126 fed to the component 104.

The second source 116 feeds the second gaseous medium 132 along the surface 106 of the component 104 via a feed line 130. The second gaseous medium 132 may be the combustion gas generated by burning a fuel such as natural gas, liquid jet fuel, liquid diesel fuel, and the like. In the illustrated embodiment, the reactant 134 in the second gaseous medium 132 is water vapor capable of rapidly volatilizing the volatilization-susceptible constituent 111 and not rapidly volatilizing the volatilization-resistant constituent 113 of the coating 110 to which the second gaseous medium 132 is contacted. In certain other embodiments, the second gaseous medium 132 may include other reactants capable of readily volatilizing the volatilization-susceptible constituent 111 and not readily volatilizing the volatilization-resistant constituent 113 of the coating 110 to which the second gaseous medium 132 is contacted. In one example, the second gaseous medium 132 may be in a temperature range from about six hundred fifty degrees Fahrenheit to about two thousand two hundred degrees Fahrenheit. In one specific example, the second gaseous medium 132 may be in the temperature range of about six hundred fifty degrees Fahrenheit to about eight hundred degrees Fahrenheit. In certain other embodiments, the second source 116 may have a valve (not shown in FIG. 2) for controlling the flow of the second gaseous medium 132 along the surface 106 of the component 104.

Figure 4A:
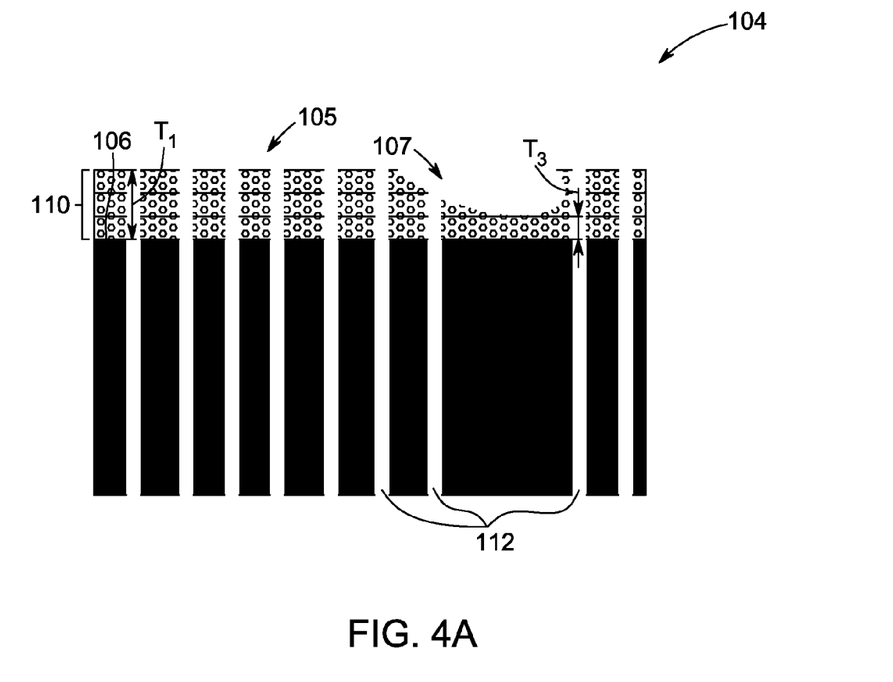
FIG. 4a is a schematic view of the component exposed to the flow of the first and second gaseous mediums in accordance with the exemplary embodiments of FIGS. 1a, 2, and 3.

In one embodiment, the measurement device 118 is configured to determine a thickness "$T_3$" (as shown in FIG. 4) of the coating 110 exposed to the flow of the first and second gaseous mediums 126, 132. In one or more embodiments, a suitable measurement device 118 includes an x-ray fluorescence detector, an energy-dispersive x-ray detector, a wavelength-dispersive x-ray detector, or an x-ray diffraction detector. Such measurement device 118, for example x-ray fluorescence and x-ray diffraction, emits photon beams 119a over the coating 110 (i.e. coated surface of the component) exposed to the flow of the first and second gaseous mediums 126, 132. In other embodiments, the measurement device 118, for example, energy-dispersive and wavelength-dispersive x-ray detectors, emits electron beams 119a over the coating 110. Further, the measurement device 118 receives a plurality of signals 119b representative of relative concentrations of the volatilization-resistant constituent 111 and the volatilization-susceptible constituent 113 of the coating 110, from the coated surface of the component 104. The measurement device 118 is further configured for processing the received plurality of signals 119b to determine the remnant thickness "$T_3$" of the coating 110. In one embodiment, the measurement device 118 is communicatively coupled to the processor-based device 122 via a network 120. It should be noted herein that the configuration of the system 100 may vary depending on the application and design criteria.

The processor-based device 122 is further communicatively coupled to the first source 114 via a first communication link 115. The processor-based device 122 controls the first source 114 for controlling a flow rate and duration of flow of the first gaseous medium 126 from the first source 114. The duration of flow of the first gaseous medium 126 may be for a predetermined period, for example, around ten minutes. Similarly, the processor-based device 122 is communicatively coupled to the second source 116 via a second communication link 117. The processor-based device 122 controls the second source 116 for controlling a flow rate and duration of flow of the second gaseous medium 132 from the second source 116. The duration of flow of the second gaseous medium 132 may be for a predetermined period, for example, around ten minutes. In such embodiments, an optimal flow rate and duration of the first and second gaseous mediums 126, 132 are maintained to accurately determine the cooling effectiveness of the component 104. In another embodiment, the measurement device 118 is external to the test device 102. In such embodiment, the measurement device 118 receives the component 104 once the experiment/testing is concluded to determine the remnant thickness of the coating 110. Similarly, the first source 114 and the second source 116 may be controlled manually by operating the respective valves (not shown in FIG. 2).

In the exemplary embodiment, the processor-based device 122 is configured to obtain the thicknesses "$T_1$", "$T_3$" (as shown in FIGS. 1a & 4a respectively) of the coating 110. The thickness "$T_1$" is an initial thickness of the coating 110 i.e. before the test. The thickness "$T_3$" is a remnant thickness of the coating 110 i.e. after the test. Specifically, the processor-based device 122 is configured to analyze a difference between the thicknesses "$T_3$", "$T_1$" to determine whether at least a portion of the coating 110 is removed from the surface 106 of the component 104 upon exposure to the first and second gaseous mediums 126, 132. The processor-based device 122 is further configured to determine an adequately cooled region and inadequately cooled region on the surface 106 of the component 104 as a step of a continuous or multistep measurement of remnant coating thickness along the surface 106 of the component 100. In another embodiment, by way of manual calculation of difference between the thicknesses "$T_3$", "$T_1$" one may determine whether at least a portion of the coating 110 is removed from the surface 106 of the component 104 upon exposure to the first and second gaseous mediums 126, 132.

In one embodiment, an extent of removal of coating 110 may be used as a measure to determine the effectiveness of film cooling the surface 106 of the component 100. In such embodiments, the variation in remnant coating thickness "$T_3$" on the surface 106 of the component 100 is a measure of the variation in cooling effectiveness as a function of location on the surface 106. The retained thickness "$T_1$" of the coating at any region on the surface is indicative of the efficacy of film cooling. The removal of most or all of the coating thickness is indicative of relatively ineffective film cooling and the retention of most or all of the coating thickness is indicative of relatively effective film cooling. Determination of the effective film cooled region and ineffective film cooled region on the surface 106 facilitates measurement of the cooling effectiveness of the component 104.

Figure 3:
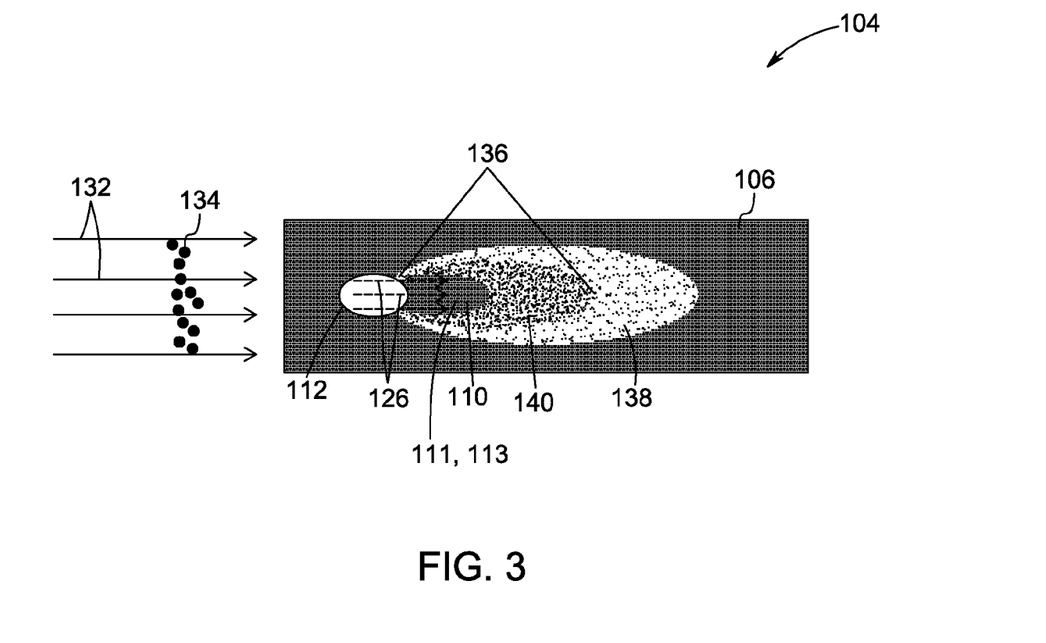
FIG. 3 is a schematic view of a surface of the component exposed to a flow of a first gaseous medium and a second gaseous medium in accordance with the exemplary embodiments of FIGS. 1a and 2.

FIG. 3 is a schematic representation of the surface 106 of the component 104 exposed to the first and second gaseous mediums 126, 132 in accordance with one exemplary embodiment. The component 104 includes the coating 110 disposed on the surface 106 and around the plurality of holes 112. The first gaseous medium 126 is fed onto the surface 106 of the component 104 through the plurality of holes 112. The first gaseous medium 126 forms a cooling film 136 over the surface 106 so as to provide cooling to the component 104. Similarly, the second gaseous medium 132 containing the reactant 134, for example, water vapor is fed along the surface 106 of the component 104. The component 104 is exposed to a flow of the first and second gaseous mediums 126, 132 for the predetermined period. The flow of the second gaseous medium 132 along the surface 106 of the component 104 results in rapid reaction of the water vapor 134 with the volatilization-susceptible constituent 111 to form a gaseous reaction product in a region of the surface 106 not covered by the cooling film 136. Similarly, the volatilization-resistant constituent 113 may react much more slowly with the water vapor 134 to form a smaller amount of gaseous reaction product in a region of the surface 106 not covered by the cooling film 136. The reaction results in volatilization of at least a portion of the volatilization-susceptible constituent 111 and the volatilization-resistant constituent 113 of the coating 110 and forms a removed portion 138 of the coating 110 on the surface 106 of the component 104. The removed portion 138 of the coating 110 has the thickness "$T_3$" i.e. remnant thickness (as shown in FIG. 4a) which is indicative of an ineffectively film cooled region when measured continual along the surface 106 of the component 100. A retained portion 140 of the coating 110 has the thickness "$T_1$" (as shown in FIG. 4a) which is indicative of an effectively film cooled region when measured across the surface 106 of the component 100. The present system and method are designed to provide a continuous measure of relatively cooling effectiveness across the surface 106 of the component 100. The terms "effectively film cooled region" and "ineffectively film cooled region" should not be construed as being limited to one particular region on the surface 106 of the component 100. The measure of effectively cooling and ineffectively cooling is over the entire surface 106 of the component 100.

In one exemplary embodiment, the second gaseous medium 132 includes water vapor that is capable of rapidly volatilizing the volatilization-susceptible constituent 111 and slowly or not volatilizing the volatilization-resistant constituent 113 that is not covered by the cooling film 136, upon exposure to the second gaseous medium 132. In such embodiment, the volume fraction or area fraction of volatilization-resistant material on the exposed surface of the coating represents the volume fraction for the remnant thickness "$T_3$" of coating 110. In some other embodiments, the second gaseous medium 132 includes oxygen or carbon-dioxide that is capable of rapidly reacting with the volatilization-susceptible constituent 111 and slowly reacting with the volatilization-resistant constituent 113 that is not covered by the cooling film 136, upon exposure to the second gaseous medium 132 to form the removed portion 138 of the coating 110.

FIG. 4a is schematic view of the component 104 exposed to the flow of first and second gaseous mediums 126, 132 in accordance with one exemplary embodiment. The component 104 exposed to the flow of first and second gaseous mediums 126, 132, is examined in the measurement device 118 to determine the thickness "$T_3$" of the coating 110. The measurement device 118 may use photons or electron beams to obtain the relative concentration of the volatilization-susceptible constituent 111 and volatilization-resistant constituent 113 for determining the thickness "$T_3$" of the coating over the entire surface 106 of the component 104. In the illustrated embodiment, the thickness "$T_1$" of the coating 110 is retained at the first region 105 of the component 104 where the volatilization-susceptible constituent 111 and volatilization-resistant constituent 113 are adequately covered by the cooling film 136 (as shown in FIG. 3). Similarly, the thickness "$T_3$" at a second region 107 of the component 104 is less than the thickness "$T_1$", where the volatilization-susceptible constituent 111 and the volatilization-resistant constituent 113 of the coating 110 are not adequately covered by the cooling film 136. In one embodiment, the thickness "$T_3$" is less than the thickness "$T_1$".

Figure 4B:
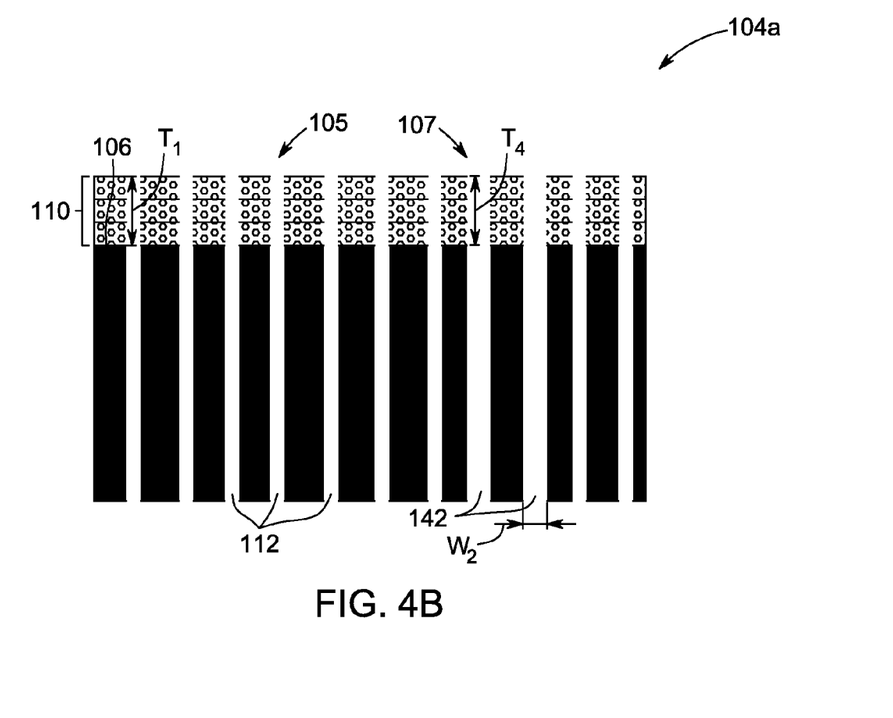

FIG. 4b is a schematic view of a redesigned component 104a including a plurality of holes 112 and a plurality of redesigned holes 142. The component 104 is redesigned to include the plurality of redesigned holes 142 at the second region 107 where the portion of the coating 110 is removed from the surface 106 of the component 104 upon exposure to the second gaseous medium 132. Specifically, the redesigned holes 142 are located in the second region 107 where the thickness "$T_3$" (as shown in FIG. 4a) of the coating 110 is substantially less than the thickness "$T_1$" of the coating 110. In the illustrated embodiment, the redesigned holes 142 have a width "$W_2$" greater than the width "$W_1$" (as shown in FIG. 1a) of the plurality of holes 112. The redesigned component 104a having the plurality of holes 112 and redesigned holes 142 is coated with the multilayer coating 110 (as shown in FIG. 1a) and exposed to the flow of the first and second gaseous mediums 126, 132. The measurement device 118 as explained with respect to the FIG. 2 is used to determine a thickness "$T_4$" of the coating 110. The coating 110 has thickness "$T_4$" equal to the thickness "$T_1$" all over the surface 106 of the redesigned component 104a to indicate that the volatilization-susceptible constituent 111 and the volatilization-resistant constituent 113 of the coating 110 are adequately covered by the cooling film 136.

Figure 5:
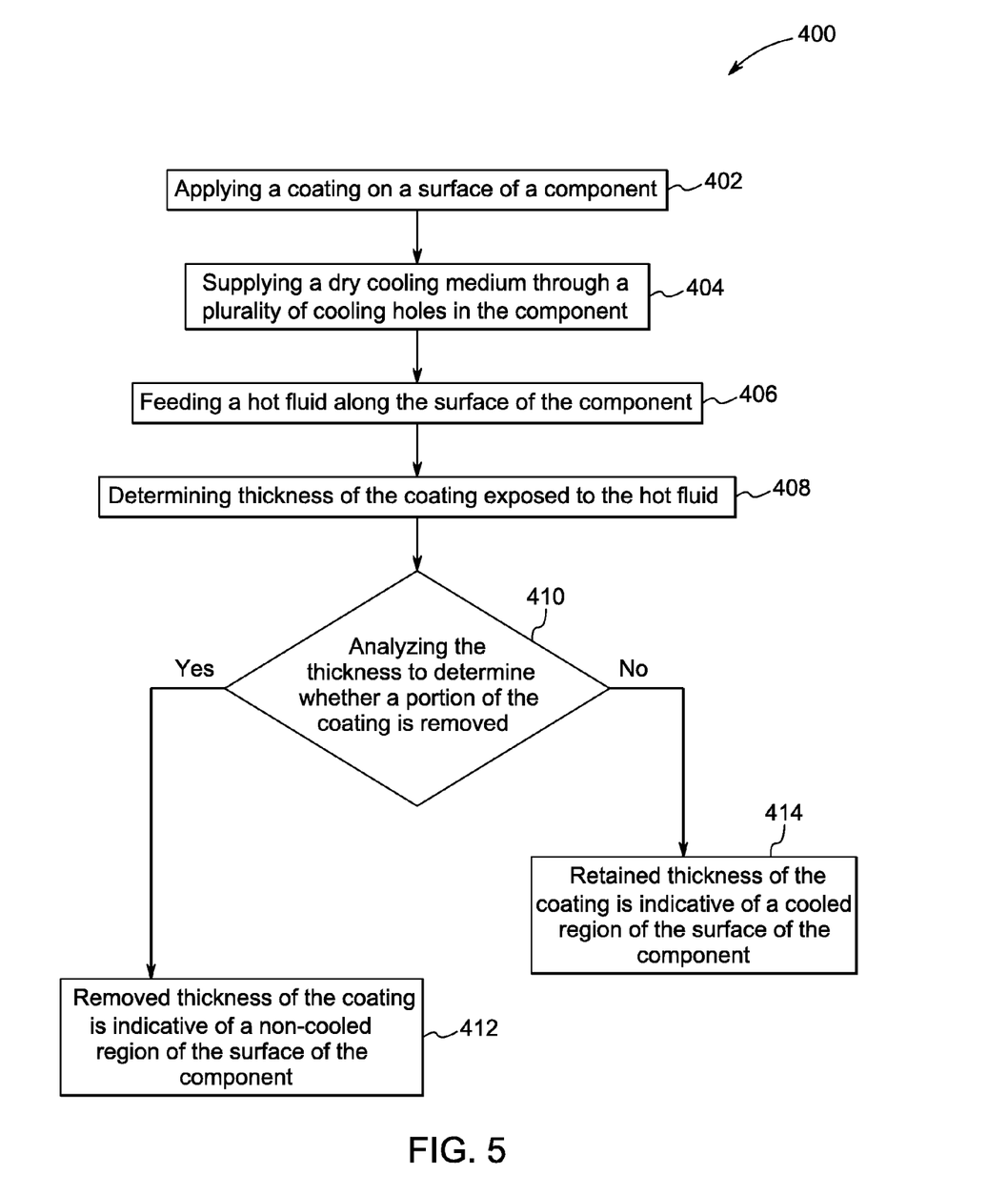
FIG. 5 is a flow chart illustrating steps involved in measuring cooling effectiveness of a component in accordance with one exemplary embodiment.

FIG. 5 is a flow chart illustrating an exemplary method 400 for measuring cooling effectiveness of a component in accordance with an exemplary embodiment.

The method 400 includes applying a coating having a volatilization-susceptible constituent and a volatilization-resistant constituent, on a surface of a component 402 in accordance with one exemplary embodiment. The coating may be a multilayer coating or a graded coating with concentrations of the volatilization-susceptible constituent and the volatilization-resistant constituent varying inversely through the thickness of the coating as a function of distance from the surface of the component. In one embodiment the volatilization-susceptible constituent may include a nitride of at least one of boron, chromium, silicon, nickel, cobalt, or an oxide of at least one of boron, chromium, silicon, nickel, cobalt, and iron. Similarly, the volatilization-resistant constituent may include an oxide of at least one of titanium, zirconium, hafnium, aluminum, yttrium, and a rare earth element. A first gaseous medium is fed through a plurality of holes in the component 404. Specifically, the first gaseous medium being a dry medium, for example, is supplied onto the surface of the component so as to form a cooling film on the surface of the component. Such a cooling film provides cooling to the surface of the component so as to prevent overheating of the component. The first gaseous medium may be air, nitrogen, argon, or the like.

A second gaseous medium is fed along the surface of the component 406. The surface of the component is exposed to a flow of the first and second gaseous mediums 408 for a predetermined period. The component may be exposed to a surface temperature in a range of 650-2200 degrees Fahrenheit. The second gaseous medium may include a reactant such as water vapor, for example. It should be noted herein that the component is not adequately cooled in regions where the coating is not adequately covered by the cooling film of the first gaseous medium. In the exemplary embodiment, the volatilization-susceptible constituent is sensitive to the reactant of the second gaseous medium. The volatilization-susceptible constituent is readily volatilized upon exposure to the second gaseous medium including the reactant, such as water vapor, to form a gaseous reaction product. The volatilization-resistant constituent is not readily volatilized upon exposure to the second gaseous medium including such reactant. The flow of the second gaseous medium along the region of the coating that is not adequately covered by the cooling film results in volatilization of the coating. The removal of the coating occurs due to the reaction of water vapor in the second gaseous medium with the volatilization-susceptible constituent of the coating. Similarly, the flow of the second gaseous medium along a region of the coating that is adequately covered by the cooling film does not result in volatilization of the coating. In one exemplary embodiment, the second gaseous medium and the first gaseous medium are supplied for a predetermined duration and at a predetermined flow rate. The supply of the first gaseous medium and the second gaseous medium above the predetermined flow rate and the duration may result in full removal of the coating. Similarly, the supply of the first gaseous medium and the second gaseous medium below the predetermined flow rate and the duration may result in partial removal of the coating. In one such embodiment, the predetermined duration may be in the range of about five to ten minutes and the predetermined flow rate may be in the range of about five cubic meters per second to eight cubic meters per second.

A measurement device may be used to determine a thickness of the coating exposed to the first and second gaseous mediums 408. The measurement device may use photons or electron beams to obtain a relative concentration of the volatilization-susceptible constituent and volatilization-resistant constituent to determine the thickness of the coating over the entire surface of the coated component. The thickness may include a final thickness of the component exposed to the flow of first and second gaseous mediums and an initial thickness of the component before exposing to the flow of the first and second gaseous mediums. The obtained thickness is analyzed via a processor-based device to determine whether at least a portion of the coating is removed from the surface of the component 410. In one embodiment, differences between the final thickness and initial thickness in one or more regions (i.e. cooled region and non-cooled region) may be an indicator to determine the cooling effectiveness of the component. In the illustrated embodiment of FIG. 4a, the first region where the coating is retained has the final thickness equal to the initial thickness which is indicative of an effectively film cooled region on the component. The second region where the coating is removed has the final thickness less than the initial thickness which is indicative of an ineffectively film cooled region on the component. The retained thickness of the coating at any region on the surface is indicative of the efficacy of film cooling. The removal of most or all of the coating thickness is indicative of relatively ineffective film cooling, i.e. a non-cooled region on the surface of the component 412. The non-cooled region is also indicative of the region of the coating that is not adequately covered by the cooling film. The retention of most or all of the coating thickness is indicative of relatively effective film cooling, i.e. a cooled region on the surface of the component 414. The cooled region is also indicative of the region of the coating that is adequately covered by the cooling film. The present system and method are designed to provide a continuous measure of relative cooling effectiveness across the surface of the component. The terms "effectively film cooled region" and "ineffectively film cooled region" should not be construed as being limited to one particular region on the surface of the component. The measure of effective cooling and ineffective cooling is over the entire surface of the component.

In one example, a multilayer coating of boron nitride and zirconium dioxide (herein also referred as "BN, $ZrO_2$") is formed on a surface of an engine component. The component is then placed in a test rig and nitrogen is fed over the surface of the component via the plurality of holes in the component so as to form a nitrogen film over the surface of the component. Further, the component is subjected to a flow of a combustion gas comprising water vapor, at a temperature of 650-

750 degrees Fahrenheit. The component may be exposed to the flow of the combustion gas and nitrogen for a predetermined period and predetermined temperature, for example, about fifteen minutes and at about 700 degrees Fahrenheit. BN is the volatilization-susceptible and ZrO2 is the volatilization-resistant constituent of the coating. The BN constituent which is not covered by the nitrogen film is removed and the ZrO2 constituent is carried away, when the water vapor in the combustion gas reacts with the coating to produce volatile products. The retained portion of the coating is not removed since such a portion is covered by the nitrogen film. Thereafter, a measurement device is used to determine the thickness of the coating exposed to the flow of combustion gas and nitrogen. The obtained thickness is analyzed to determine the ineffectively film cooled regions and effectively film cooled regions on the engine component so as to measure the effectiveness of the cooling holes in the component.

Embodiments of the present invention discussed herein facilitate an easy and economical method of determining the effectiveness of cooling holes disposed on the surface of the component, in a relatively low temperature test rig or under engine operating conditions. Further, the embodiments facilitate accurate design of such holes, as the techniques are based on the identified surfaces of the component which are subjected to volatilization of the volatilization-susceptible constituent and the volatilization-resistant constituent of the coating.

While only certain features of embodiments have been illustrated and described herein, many modifications and changes will occur to those skilled in the art. It is therefore to be understood that the appended claims are intended to cover all such modifications and changes as falling within the spirit of the invention.

The invention claimed is:

1. A method for measuring cooling effectiveness of a component, the method comprising:
    providing the component having a surface provided with a coating including a volatilization-susceptible constituent and a volatilization-resistant constituent;
    supplying a first gaseous medium from a first source, through a plurality of holes in the component, for forming a cooling film of the first gaseous medium on the surface;
    feeding a second gaseous medium from a second source, along the surface of the component;
    exposing the component to a flow of the first and second gaseous mediums for a predetermined period;
    determining a thickness of the coating exposed to the flow of the first and second gaseous mediums from a measurement device; and
    analyzing the thickness of the coating to determine whether at least a portion of the coating is removed from the surface of the component upon exposure to the first and second gaseous mediums for the predetermined period, wherein a removed thickness of the coating is indicative of an ineffectively film cooled region on the surface of the component and a retained thickness of the coating is indicative of an effectively film cooled region on the surface of the component.

2. The method of claim 1, wherein the volatilization-susceptible constituent comprises a nitride of at least one of boron, chromium, silicon, nickel, cobalt, and iron, or an oxide of at least one of boron, chromium, silicon, nickel, cobalt, and iron.

3. The method of claim 1, wherein the volatilization-resistant constituent comprises an oxide of at least one of titanium, zirconium, hafnium, aluminum, yttrium, and a rare earth element.

4. The method of claim 1, wherein the volatilization-susceptible constituent has a concentration in a range from about 10 percent to about 90 percent by volume and the volatilization-resistant constituent has a concentration in a range from about 90 percent to about 10 percent by volume, and wherein the concentrations of the volatilization-susceptible constituent and volatilization-resistant constituent vary inversely over a thickness of the coating as a function of distance from the surface of the component.

5. The method of claim 4, wherein the coating comprises at least one of a multilayer coating and a gradient coating, and wherein the coating is applied using at least one of a chemical vapor deposition (CVD) technique and a physical vapor deposition (PVD) technique.

6. The method of claim 1, wherein the component comprises at least one of a gas turbine component and an aircraft engine component.

7. The method of claim 1, wherein the first gaseous medium is a dry medium comprising at least one of air, nitrogen, and argon.

8. The method of claim 1, wherein the second gaseous medium is a combustion gas having a reactant that reacts with at least a portion of the volatilization-susceptible constituent of the coating to form a gaseous reaction product, and wherein the first gaseous medium does not contain the reactant.

9. The method of claim 8, wherein the reactant is at least one of oxygen, carbon dioxide, water vapor, and a species of gaseous halide.

10. The method of claim 9, further comprising volatilizing the portion of the volatilization-susceptible constituent and volatilization-resistant constituent of the coating at a different rate, upon exposure to the reactant of the second gaseous medium so as to remove the portion of the coating from the surface of the component.

11. The method of claim 8, wherein the second gaseous medium comprises water vapor in the range from about 1 percent to about 100 percent by volume.

12. The method of claim 1, wherein the exposing comprises exposure of the component by maintaining a surface temperature of the component in a range from about 650 to about 2200 degrees Fahrenheit.

13. The method of claim 1, wherein the determining comprises:
    emitting at least one of photons, and electron beams onto the coated surface of the component exposed to the flow of the first and second gaseous mediums;
    receiving a plurality of signals representative of a relative concentration of the volatilization-resistant constituent and the volatilization-susceptible constituent of the coating, from the coated surface of the component; and
    processing the received plurality of signals to determine the thickness of the coating.

14. The method of claim 1, further comprising controlling the first source to control a flow rate and duration of flow of the first gaseous medium from the first source.

15. The method of claim 1, further comprising controlling the second source to control a flow rate and duration of flow of the second gaseous medium from the second source.

16. The method of claim 1, further comprising redesigning the cooling holes if at least the portion of the coating is removed from the surface of the component upon exposure to the second gaseous medium.

17. The method of claim 16, wherein the redesigning comprises altering at least one of a location, dimension, and number of the cooling holes in the component.

18. The method of claim 17, further comprising supplying the first gaseous medium through a plurality of redesigned cooling holes in the component such that a uniform cooling film is formed over the surface of the component and removal of the coating from the surface of the component is prevented.

19. A method for measuring cooling effectiveness, the method comprising:
provic ing the component having a surface provided with a coating including a volatilization-susceptible constituent and a volatilization-resistant constituent;
supplying a first gaseous medium from a first source, through a plurality of holes in the component for a predetermined period, for forming a cooling film of the first gaseous medium on the surface;
feeding a second gaseous medium from a second source, along the surface of the component for the predetermined period and volatize at least a portion of the coating upon exposure to the second gaseous medium to form a removed portion of the coating;
determining a thickness of the coating exposed to a flow of the first and second gaseous mediums for the predetermined period; and
analyzing the thickness of the coating for a removed thickness of the coating that is indicative of an ineffectively film cooled region on the surface of the component and for a retained thickness of the coating that is indicative of an effectively film cooled region on the surface of the component.

20. A system comprising:
a first source for supplying a first gaseous medium through a plurality of holes in a component, said component having a surface provided with a coating including a volatilization-susceptible constituent and a volatilization-resistant constituent;
a second source for supplying a second gaseous medium along the surface of the component;
a measurement device for determining a thickness of the coating exposed to the first and second gaseous mediums for a predetermined period; and
a processor-based device communicatively coupled to the measurement device, wherein the processor-based device is configured to:
receive the thickness from the measurement device; and
analyze the obtained thickness to determine whether at least a portion of the coating is removed from the surface of the component upon exposure to the first and second gaseous mediums, wherein a removed thickness of the coating is indicative of an ineffectively film cooled region on the surface of the component and a retained thickness of the coating is indicative of an effectively film cooled region on the surface of the component.

21. The system of claim 20, wherein the system comprises a test device for housing the component, the first source, and the second source.

22. The system of claim 20, further comprising a coating device for providing the coating having at least one of a multilayer coating and a graded coating on the surface of the component by at least one of a chemical vapor deposition (CVD) technique and a physical vapor deposition (PVD) technique.

23. The system of claim 22, wherein the volatilization-susceptible constituent has a concentration in a range from about 10 percent to about 90 percent by volume and the volatilization-resistant constituent has a concentration in a range from about 90 percent to about 10 percent by volume, and wherein the concentrations of the volatilization-susceptible constituent and volatilization-resistant constituent vary inversely over a thickness of the coating as a function of distance from the surface of the component.

24. The system of claim 20, wherein the measurement device comprises at least one of an x-ray fluorescence detector, an energy-dispersive x-ray detector, a wavelength-dispersive x-ray detector, and an x-ray diffraction detector.

* * * * *